(12) United States Patent
Hiraoka

(10) Patent No.: US 12,408,894 B2
(45) Date of Patent: Sep. 9, 2025

(54) ULTRASOUND ENDOSCOPE

(71) Applicant: OLYMPUS CORPORATION, Tokyo (JP)

(72) Inventor: Jin Hiraoka, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 454 days.

(21) Appl. No.: 17/864,811

(22) Filed: Jul. 14, 2022

(65) Prior Publication Data

US 2022/0361846 A1 Nov. 17, 2022

Related U.S. Application Data

(63) Continuation of application No. PCT/JP2020/005735, filed on Feb. 14, 2020.

(51) Int. Cl.
*A61B 1/00* (2006.01)
*A61B 8/00* (2006.01)
*A61B 8/12* (2006.01)

(52) U.S. Cl.
CPC ............. *A61B 8/445* (2013.01); *A61B 8/12* (2013.01)

(58) Field of Classification Search
CPC ....... A61B 8/445; A61B 8/12; A61B 1/00082; A61B 2017/22048; A61B 2017/22051; A61B 2017/22065; A61B 17/2202
USPC .................................. 600/156, 116; 604/509
See application file for complete search history.

(56) References Cited

U.S. PATENT DOCUMENTS

| | | | | |
|---|---|---|---|---|
| 5,471,988 A | * | 12/1995 | Fujio | A61B 8/445 601/3 |
| 2003/0060813 A1 | * | 3/2003 | Loeb | A61B 18/24 606/17 |
| 2004/0082883 A1 | * | 4/2004 | Kohno | A61B 1/05 601/2 |
| 2008/0200816 A1 | * | 8/2008 | Fujimura | A61B 1/042 600/472 |

(Continued)

FOREIGN PATENT DOCUMENTS

| | | |
|---|---|---|
| JP | 2004-209044 A | 7/2004 |
| JP | 2020-000647 A | 1/2020 |
| WO | 2019/031465 A1 | 2/2019 |

OTHER PUBLICATIONS

International Search Report dated Apr. 14, 2020 received in PCT/JP2020/005735.

*Primary Examiner* — Anh Tuan T Nguyen
*Assistant Examiner* — James Edward Boice
(74) *Attorney, Agent, or Firm* — Scully, Scott, Murphy & Presser, P.C.

(57) ABSTRACT

An ultrasound endoscope includes: a balloon suction duct that is provided inside an insertion portion and that is where liquid inside a balloon is suctioned through, the balloon covering an ultrasound transducer positioned at a distal end of the insertion portion; a rigid portion that includes a balloon groove and an end surface positioned at an end portion of the rigid portion, the end portion being on a distal end side of the balloon groove, the end surface being a surface intersecting a longitudinal direction of the insertion portion, the end surface having an opening formed thereon, the opening communicating with the balloon suction duct; and a holder that is positioned on a distal end side of the rigid portion, the holder being configured to hold the ultrasound transducer.

18 Claims, 10 Drawing Sheets

(56) References Cited

U.S. PATENT DOCUMENTS

2015/0231378 A1* 8/2015 Pepper .................. A61M 29/02
606/194

* cited by examiner

ULTRASOUND ENDOSCOPE

CROSS-REFERENCE TO RELATED APPLICATION

This application is a continuation of International Application No. PCT/JP2020/005735, filed on Feb. 14, 2020, the entire contents of which are incorporated herein by reference.

BACKGROUND

1. Technical Field

The present disclosure relates to ultrasound endoscopes.

2. Related Art

In the related art, liquid, such as degassed water, is injected into a balloon attached to an ultrasound endoscope having an ultrasound transducer at a distal end of an insertion portion inserted into a subject, the balloon covering the outer periphery of the ultrasound transducer, and the balloon is brought into close contact with an observed region, such as the digestive tract (see, for example, Japanese Laid-open Patent Publication No. 2004-209044). After observation, the liquid in the balloon is suctioned from the inside of the balloon via a balloon suction duct that has been inserted inside the insertion portion.

SUMMARY

In some embodiments, an ultrasound endoscope includes: a balloon suction duct that is provided inside an insertion portion to be inserted into a subject and that is where liquid inside a balloon is suctioned through, the balloon covering an ultrasound transducer positioned at a distal end of the insertion portion; a rigid portion that includes a balloon groove to which a band of the balloon is attachable, and an end surface positioned at an end portion of the rigid portion, the end portion being on a distal end side of the balloon groove, the end surface being a surface intersecting a longitudinal direction of the insertion portion, the end surface having an opening formed thereon, the opening communicating with the balloon suction duct; and a holder that is positioned on a distal end side of the rigid portion, the holder being configured to hold the ultrasound transducer, the holder including a distal end portion having a first outer diameter, and a proximal end portion having a second outer diameter smaller than the first outer diameter, the proximal end portion being arranged adjacently to the opening.

The above and other features, advantages and technical and industrial significance of this disclosure will be better understood by reading the following detailed description of presently preferred embodiments of the disclosure, when considered in connection with the accompanying drawings.

DETAILED DESCRIPTION

Embodiments of an ultrasound endoscope according to the disclosure will be described hereinafter by reference to the drawings. The disclosure is not limited by these embodiments. The disclosure may be applied generally to ultrasound endoscopes that enable observation using balloons.

Any elements that are the same or corresponding to each other are assigned with the same reference sign throughout the drawings, as appropriate. It also needs to be noted that the drawings are schematic, and relations between dimensions of each element therein and proportions between the elements therein may be different from the actual ones. The drawings may also include a portion that differs in its dimensional relations or proportions between the drawings.

Embodiments

Configuration of Ultrasound Endoscope

Figure 1:
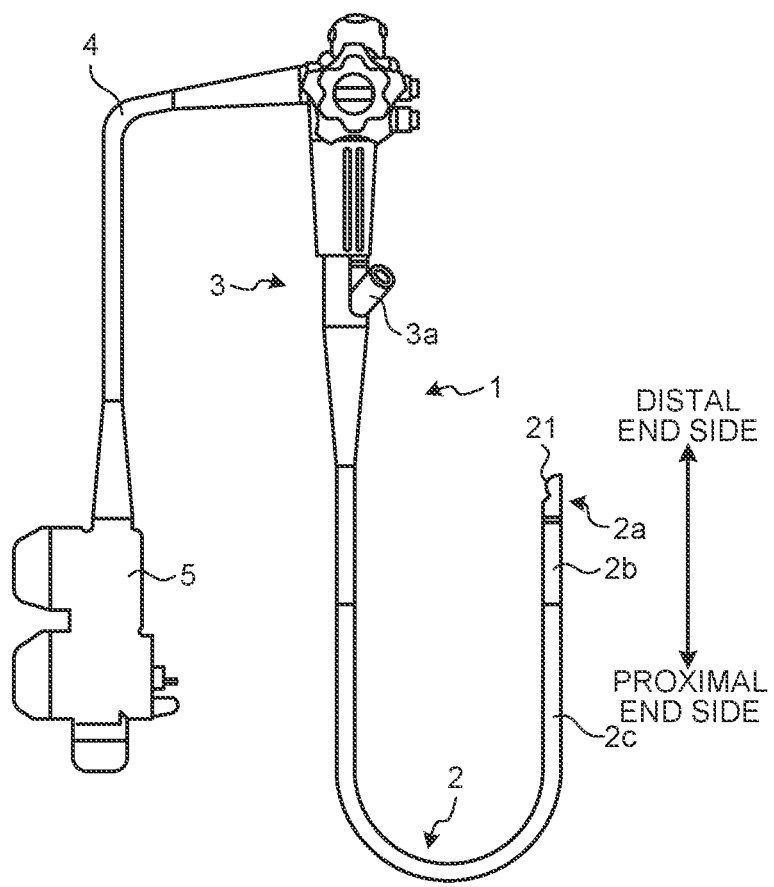
FIG. 1 is a schematic diagram illustrating a configuration of an ultrasound endoscope according to an embodiment.

FIG. 1 is a schematic diagram illustrating a configuration of an ultrasound endoscope according to an embodiment. An ultrasound endoscope 1 includes: an insertion portion 2 that has an imaging portion provided at a distal end of the insertion portion 2 and that is inserted into a subject; an operating portion 3 that is provided consecutively to the insertion portion 2 on a proximal end side of the insertion portion 2; a universal cord 4 extending from a side portion of the operating portion 3; and a connector 5 that is provided consecutively to the universal cord 4 and is connected to devices, such as: an observation device that controls the ultrasound endoscope 1; and a light source device for supply of illumination light to the ultrasound endoscope 1. In this specification, as illustrated in FIG. 1, a distal end side (away from the operating portion 3) will be referred to as the "distal end side" and a proximal end side (toward the operating portion 3) will be referred to as the "proximal end side", the distal end side and proximal end side being along a longitudinal direction of the ultrasound endoscope 1.

The ultrasound endoscope 1 is an ultrasound endoscope for bronchi or digestive tracts.

The insertion portion 2 has, in order from the distal end side, a distal end portion 2a, a bending portion 2b configured to be bendable according to operation of the operating portion 3, and a flexible tube portion 2c having flexibility. A proximal end of the flexible tube portion 2c is provided consecutively to the operating portion 3 on the distal end side of the operating portion 3.

The operating portion 3 has a forceps insertion opening 3a provided for insertion of, for example, a forceps needle, which is a treatment tool. A forceps insertion passage is provided inside the insertion portion 2 and the forceps insertion opening 3a serves as an insertion opening of the forceps insertion passage. That is, the ultrasound endoscope 1 is an endoscope through which a treatment tool is able to be inserted.

Configuration of Distal End Portion of Ultrasound Endoscope

Figure 2:
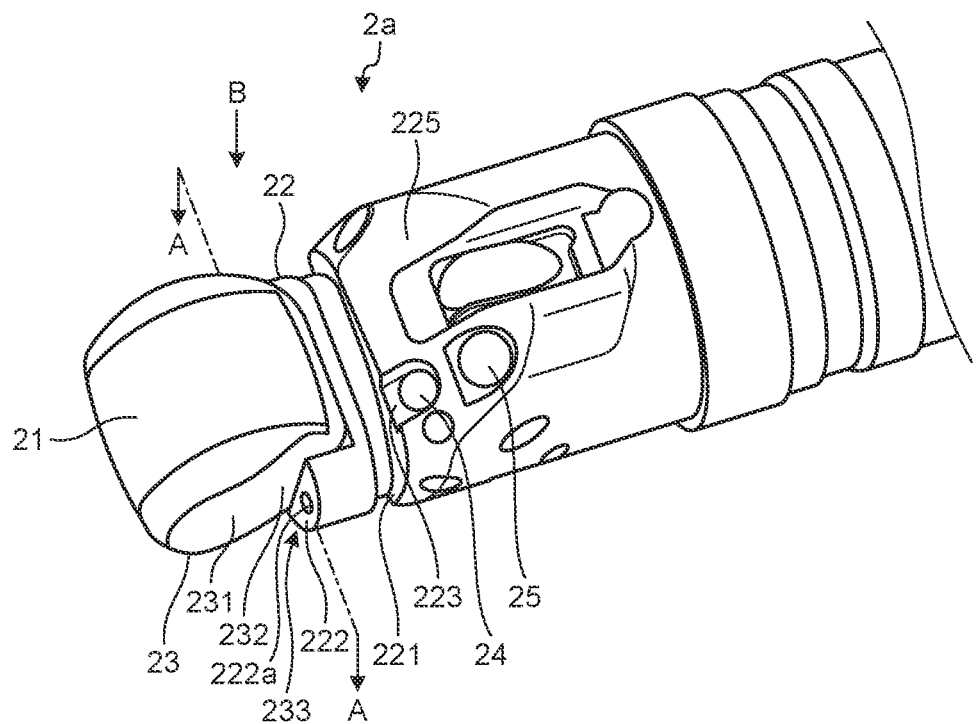
FIG. 2 is a perspective view of a distal end portion of the ultrasound endoscope illustrated in FIG. 1.
Figure 3:
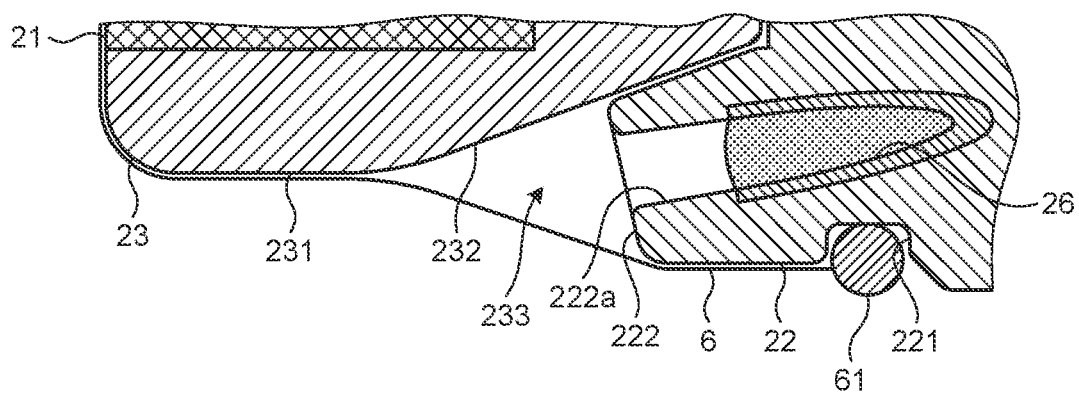
FIG. 3 is a partial sectional view corresponding to a line A-A in FIG. 2.

FIG. 2 is a perspective view of a distal end portion of the ultrasound endoscope illustrated in FIG. 1. The ultrasound endoscope 1 has an ultrasound transducer 21, a rigid portion 22, a holder 23, an illumination lens 24, and an objective lens 25. FIG. 3 is a partial sectional view corresponding to a line A-A in FIG. 2. The ultrasound endoscope 1 includes a balloon suction duct 26. FIG. 3 illustrates a balloon 6 that has been attached to the distal end of the insertion portion 2 to cover the ultrasound transducer 21.

The ultrasound transducer 21 is a convex ultrasound transducer and has plural piezoelectric elements regularly arrayed to form a convex circular arc. The ultrasound transducer 21 may be not necessarily a convex ultrasound transducer and may be a linear ultrasound transducer instead. The ultrasound transducer 21 converts a pulse signal input from an ultrasound observation device into ultrasound pulses and transmits the ultrasound pulses into a subject. Furthermore, the ultrasound transducer 21 converts ultrasound echoes reflected in the subject into an electric echo signal and outputs the electric echo signal to the ultrasound observation device.

The rigid portion 22 has a balloon groove 221, a first surface 222, and a stepped portion 223. A band 61 of the balloon 6 is attachable to the balloon groove 221. The first surface 222 is a surface that is positioned on the distal end side of the balloon groove 221 and that is along a direction intersecting a longitudinal direction of the insertion portion 2, and has an opening 222a formed thereon, the opening 222a communicating with the balloon suction duct 26 along a direction in which the balloon suction duct 26 extends. A plane in which the opening 222a is open is along a direction intersecting the longitudinal direction of the insertion portion 2, as illustrated in FIG. 3. Furthermore, the first surface 222 and an end portion of the opening 222a are approximately orthogonal to each other. This is because a brush that has jutted out from the opening 222a may be damaged if an angle formed by the first surface 222 and the end portion of the opening 222a is an acute angle.

Figure 4:
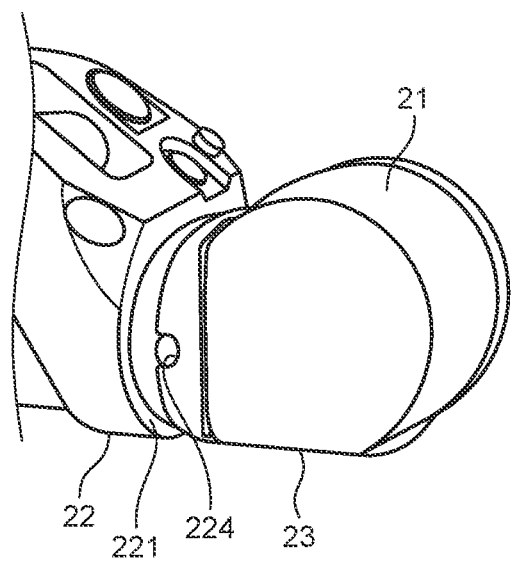
FIG. 4 is a perspective view of the ultrasound endoscope illustrated in FIG. 2 as viewed from an opposite side opposite to a side where an opening is.

FIG. 4 is a perspective view of the ultrasound endoscope illustrated in FIG. 2 as viewed from an opposite side opposite to a side where an opening is. As illustrated in FIG. 4, the rigid portion 22 has an opening 224 formed therein. The opening 224 is positioned on the distal end side of the balloon groove 221 and communicates with a balloon water feeding duct through which liquid is fed into the balloon 6 covering the ultrasound transducer 21. The opening 224 may be formed such that part of the opening 224 is in the balloon groove 221, as long as the opening 224 is at a position where the opening 224 is completely covered by the balloon 6 when the balloon 6 has been attached.

Figure 5:
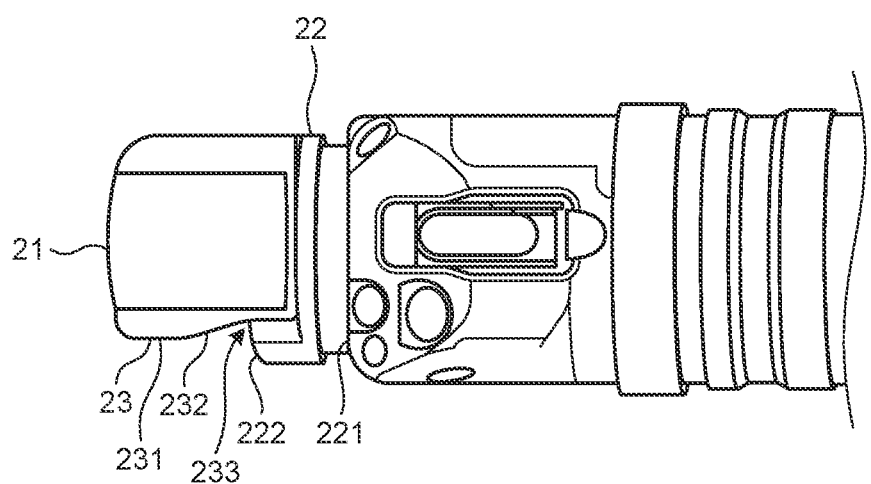
FIG. 5 is a view of the ultrasound endoscope illustrated in FIG. 2, the view being taken in a direction indicated by an arrow B.

The holder 23 is positioned on the distal end side of the rigid portion 22 and holds the ultrasound transducer 21. FIG. 5 is a view of the ultrasound endoscope illustrated in FIG. 2, the view being taken in a direction indicated by an arrow B. As illustrated in FIG. 5, the holder 23 has a second surface 231 along the longitudinal direction of the insertion portion 2, and a third surface 232 continuous with the second surface 231 and along a direction intersecting the longitudinal direction of the insertion portion 2. The first surface 222 and the third surface 232 are approximately orthogonal to each other. Being approximately orthogonal herein means that an angle formed between the first surface 222 and the third surface 232 is, for example, 600 or larger, and this angle is more preferably 80° or larger. A space 233 has been formed between the balloon 6, the first surface 222, and the third surface 232. This space 233 is formed on the distal end side of the opening 222a and extends to the opening 222a in a direction orthogonal to the longitudinal direction of the insertion portion 2. Furthermore, the space 233 is continuous along and a direction (a direction orthogonal to the plane of paper of FIG. 3) orthogonal to both of the longitudinal direction and the direction in which the balloon suction duct 26 extends.

The illumination lens 24 irradiates the inside of the subject with illumination light emitted by the light source device via a light guide. The illumination lens 24 has, formed on its surface, a chamfered portion that has been slightly chamfered. The illumination lens 24 is positioned at the stepped portion 223 that is a depressed portion formed on a sloped surface 225. In other words, the illumination lens 24 is positioned at the stepped portion 223 that has been stepped lower than the objective lens 25 formed on the sloped surface 225. As a result, light output from the chamfered portion of the illumination lens 24 is prevented from: being incident on the objective lens 25; and thereby causing flare. Therefore, there is no need for application of a black adhesive, for example, to the chamfered portion of the illumination lens 24 to cover the chamfered portion for prevention of flare, and workability will thus be improved and the field of view will not be hindered by such an adhesive. Furthermore, the stepped portion 223 is a depressed portion that is open at the distal end side. As a result, liquid that has adhered to the illumination lens 24, for example, will flow out from the side that is open without staying in the stepped portion 223 and this prevents scattering of the illumination light due to the liquid.

The objective lens 25 has been formed on the sloped surface 225. The objective lens 25 condenses light reflected inside the subject and forms an image on an imaging plane of an imaging element. An image signal generated in the imaging element is transmitted to an endoscope observation device via a signal cable.

The balloon suction duct 26 is provided inside the insertion portion 2 inserted into the subject. Liquid inside the balloon 6 covering the ultrasound transducer 21 positioned at the distal end of the insertion portion 2 is suctioned through this balloon suction duct 26.

The embodiment described above enables a distal end of the brush inserted from the proximal end side to jut out from the opening 222a because the opening 222a is formed along the direction in which the balloon suction duct 26 extends. Therefore, workability for washing the ultrasound endoscope 1 is improved because the brush inserted into the balloon suction duct 26 from the proximal end side is able to be jutted out from the opening 222a and the inside of the balloon suction duct 26 is thereby able to be washed.

Furthermore, because the space 233 has been formed in this embodiment, the balloon 6 is prevented from being stuck to the opening 222a and thus from failing to be deflated when liquid inside the balloon 6 is suctioned through the balloon suction duct 26.

Furthermore, in this embodiment, the space 233 is continuous along the direction (the direction orthogonal to the plane of paper of FIG. 3) orthogonal to both of the longitudinal direction and the direction in which the balloon suction duct 26 extends. As a result, liquid in the balloon 6 flows into the opening 222a from both of the directions along which the space 233 is continuous and the balloon 6 is thus prevented from sticking to the opening 222a. The first surface 222 and the third surface 232 are preferably approximately orthogonal to each other for liquid in the balloon 6 to more easily flow into the opening 222a.

Furthermore, in this embodiment, at least part of the first surface 222 is preferably positioned outward relative to the holder 23 as viewed from the distal end side of the insertion portion 2. Positioning part of the first surface 222 more outward than the holder 23 forms a level difference between the first surface 222 and the holder 23 and thus prevents the balloon 6 from sticking to the opening 222a.

Furthermore, in this embodiment, at least part of the opening 222a is preferably positioned outward relative to the holder 23 as viewed from the distal end side of the insertion portion 2. Positioning part of the opening 222a more outward than the holder 23 prevents: the brush, which has jutted out from the opening 222a, from bumping against the holder 23; and movement of the brush from being hindered, and workability for washing is thus improved. Similarly, in this embodiment, the brush, which has jutted out from the opening 222a, is prevented from bumping against the holder 23, movement of the brush is thus prevented from being hindered, and workability for washing is thus improved, because the opening 222a is open in the plane along the direction intersecting the longitudinal direction (the left-right direction in FIG. 3) of the insertion portion 2.

First Modified Example

Figure 6:
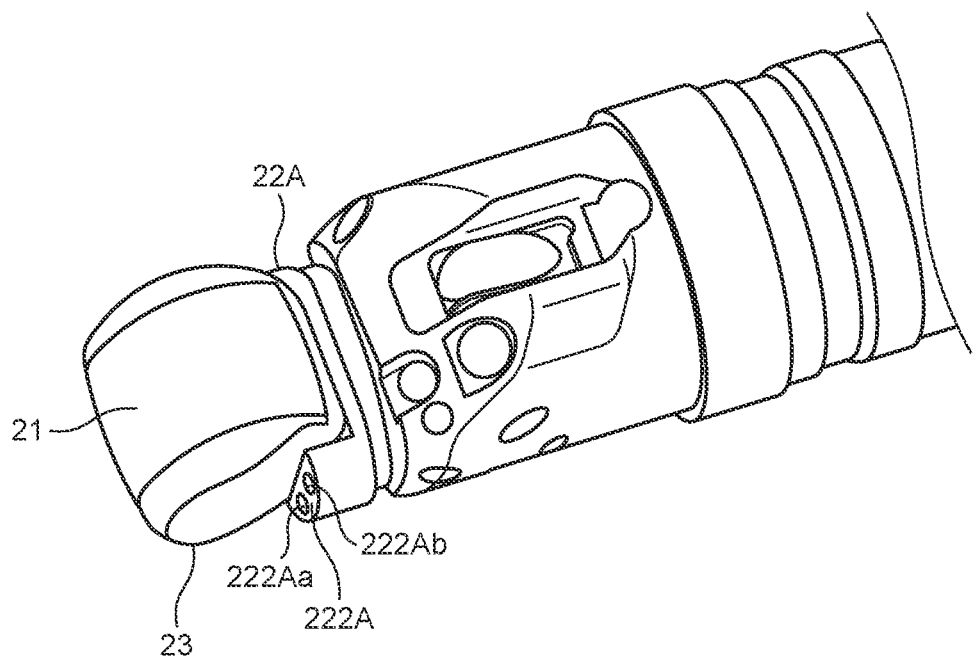
FIG. 6 is a perspective view of a distal end portion of an ultrasound endoscope according to a first modified example.

FIG. 6 is a perspective view of a distal end portion of an ultrasound endoscope according to a first modified example. As illustrated in FIG. 6, an opening 222Aa communicating with a balloon suction duct and an opening 222Ab communicating with a balloon water feeding duct have been formed on a first surface 222A of a rigid portion 22A. The opening 222Aa of the balloon suction duct and the opening 222Ab of the balloon water feeding duct may be provided on one side as illustrated. This first modified example enables washing by allowing a brush to be jutted out from the opening 222Aa or the opening 222Ab for both the balloon suction duct and the balloon water feeding duct.

Second Modified Example

Figure 7:
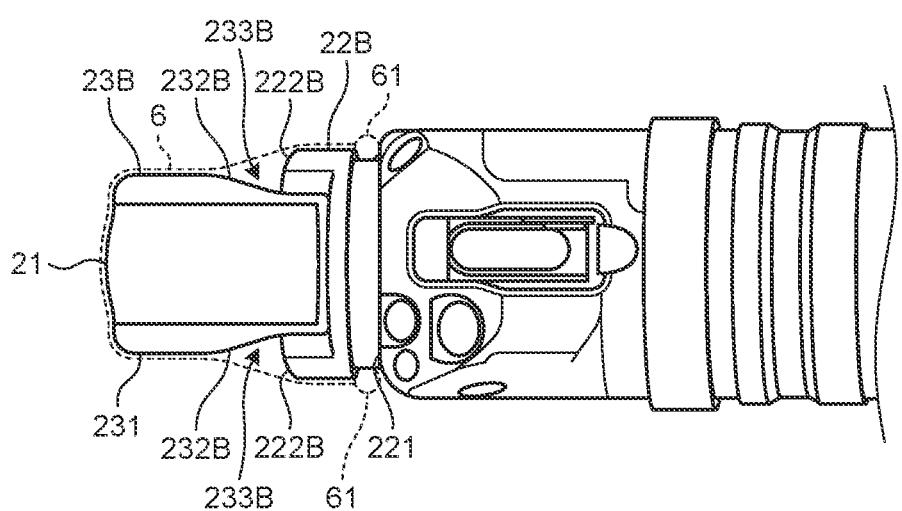
FIG. 7 is a top view of a distal end portion of an ultrasound endoscope according to a second modified example.

FIG. 7 is a top view of a distal end portion of an ultrasound endoscope according to a second modified example. FIG. 7 illustrates, with a broken line, a cross section of a balloon 6 that has been attached to a distal end of an insertion portion 2. As illustrated in FIG. 7, a first surface 222B has been formed on both sides of a rigid portion 22B. An opening communicating with a balloon suction duct has been formed on the first surface 222B, which is on one side, and an opening communicating with a balloon water feeding duct has been formed on the first surface 222B, which is on the other side. Furthermore, a third surface 232B and a space 233B have been formed on both sides of a holder 23B. This second modified example enables washing by allowing a brush to be jutted out from the opening for both the balloon suction duct and the balloon water feeding duct.

An example where the rigid portion 22 and the holder 23 are separately bodied has been described above with respect to the embodiment, but the rigid portion 22 and the holder 23 may be formed integrally with each other.

Furthermore, an example where the balloon suction duct and the balloon water feeding duct are provided separately has been described above with respect to the embodiment, but one duct may have functions of both the balloon suction duct and the balloon water feeding duct.

Configuration of Bending Portion of Ultrasound Endoscope

Figure 8:
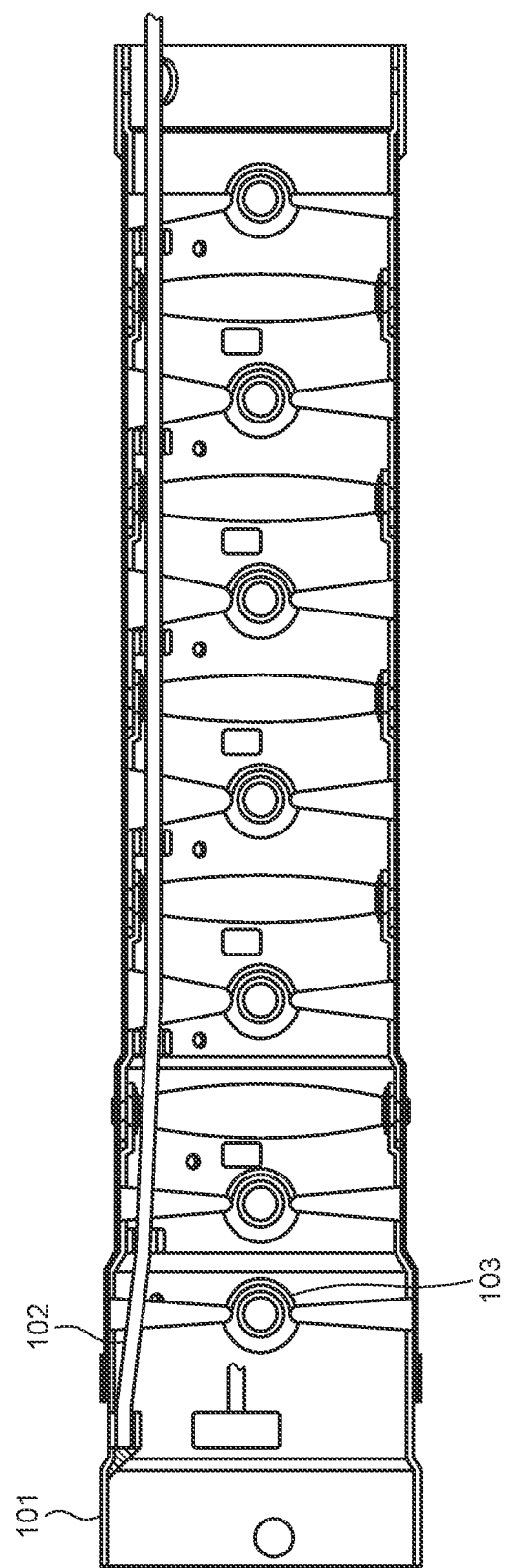
FIG. 8 is an enlarged sectional view of bending pieces of a bending portion.

FIG. 8 is an enlarged sectional view of bending pieces of a bending portion. As illustrated in FIG. 8, the bending portion 2b has a first piece 101 positioned at a distal end of the bending portion 2b, an operating wire 102 that transmits operation received by the operating portion 3 to the bending portion 2b, and a rivet 103 that bendably connects bending pieces together.

Figure 9:
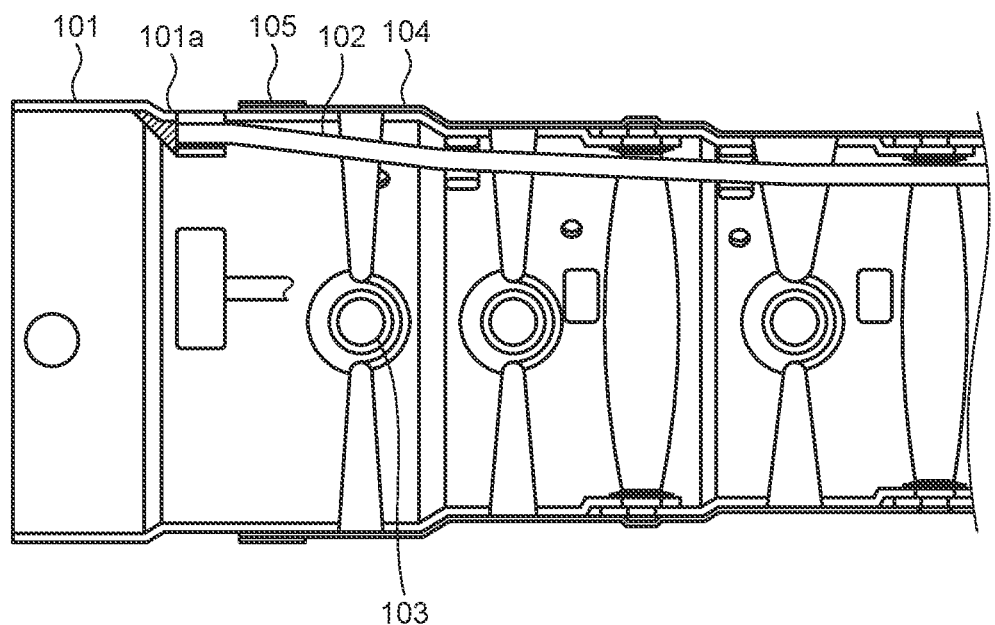
FIG. 9 is an enlarged view of a distal end portion in FIG. 8.

FIG. 9 is an enlarged view of a distal end portion in FIG. 8. As illustrated in FIG. 9, the bending portion 2b has a blade 104 covering the outer periphery of the bending portion 2b, and a blade end fixing portion 105 that fixes a distal end of the blade 104 to the first piece 101. Furthermore, the first piece 101 has a small diameter portion 101a having a small diameter than a distal end portion of the first piece 101, the distal end portion having the largest diameter. The blade end fixing portion 105 is positioned at the small diameter portion 101a. As a result, the bending portion 2b is able to be reduced in diameter and strain on the patient at the time of insertion is able to be reduced, as compared to a case where the blade end fixing portion 105 is positioned at the distal end portion of the first piece 101, the distal end portion having the largest diameter.

Figure 10:
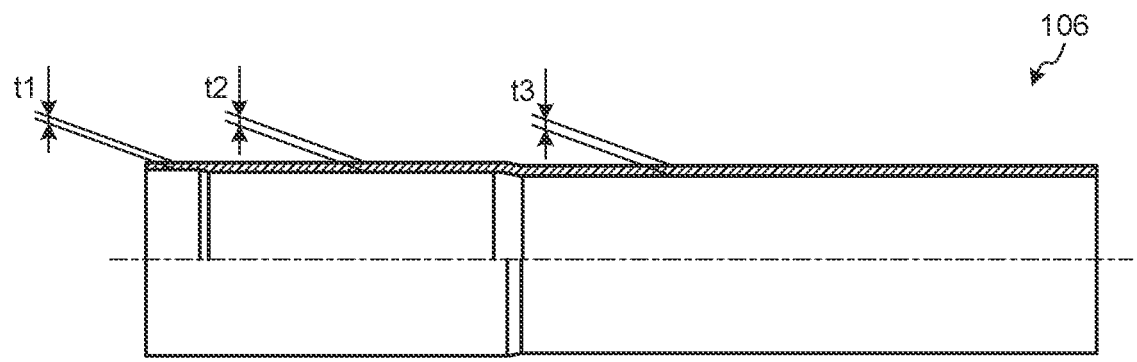
FIG. 10 is an enlarged sectional view of bending rubber.

FIG. 10 is an enlarged sectional view of bending rubber. Although not illustrated in FIG. 9, bending rubber 106 is attached to the outer periphery of the blade 104 and keeps the inside of the insertion portion 2 watertight. As illustrated in FIG. 10, thicknesses t1, t2, and t3 of the bending rubber 106 have a relation, $t1<t2<t3$. A portion of the bending rubber 106, the portion having the thickness t1, corresponds to the distal end portion of the first piece 101, the distal end portion having the largest diameter. A portion of the bending rubber 106, the portion having the thickness t2, corresponds to the small diameter portion 101a and a portion on the proximal end side of the small diameter portion 101a. A portion of the bending rubber 106, the portion having the thickness t3, corresponds to a portion that is at the proximal end side and that is uniform in thickness.

The bending portion 2b is preferably bent uniformly from the proximal end side to the distal end upon bending operation. However, in a case where bending rubber is uniform in thickness, the proximal end side tends to be bent more. Therefore, the bending rubber 106 is configured such that the bending portion 2b is bent uniformly from the proximal end side to the distal end upon bending operation, by adjustment of the thickness of the bending rubber 106.

Figure 11:
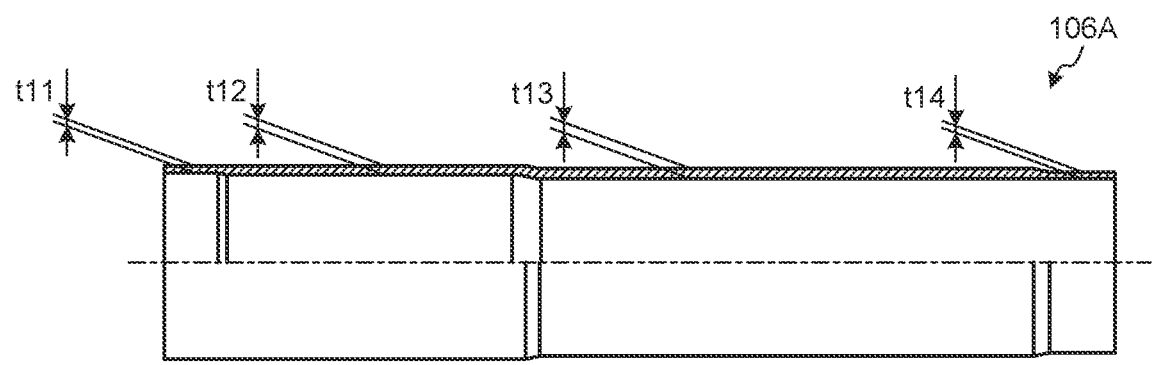
FIG. 11 is an enlarged sectional view of bending rubber.

FIG. 11 is an enlarged sectional view of bending rubber. As illustrated in FIG. 11, in this modified example, thicknesses t11, t12, t13, and t14 of bending rubber 106A have relations, $t11<t12$ and $t14<t13$. A portion of the bending rubber 106A, the portion having the thickness t14, corresponds to a proximal end portion of the blade 104, the proximal end portion being a portion to be fixed to the first piece 101. The proximal end side of the bending rubber 106A may thus be made thin and the bending portion 2b may thereby be reduced in diameter.

Internal Configuration of Distal End Portion of Ultrasound Endoscope

Figure 12:
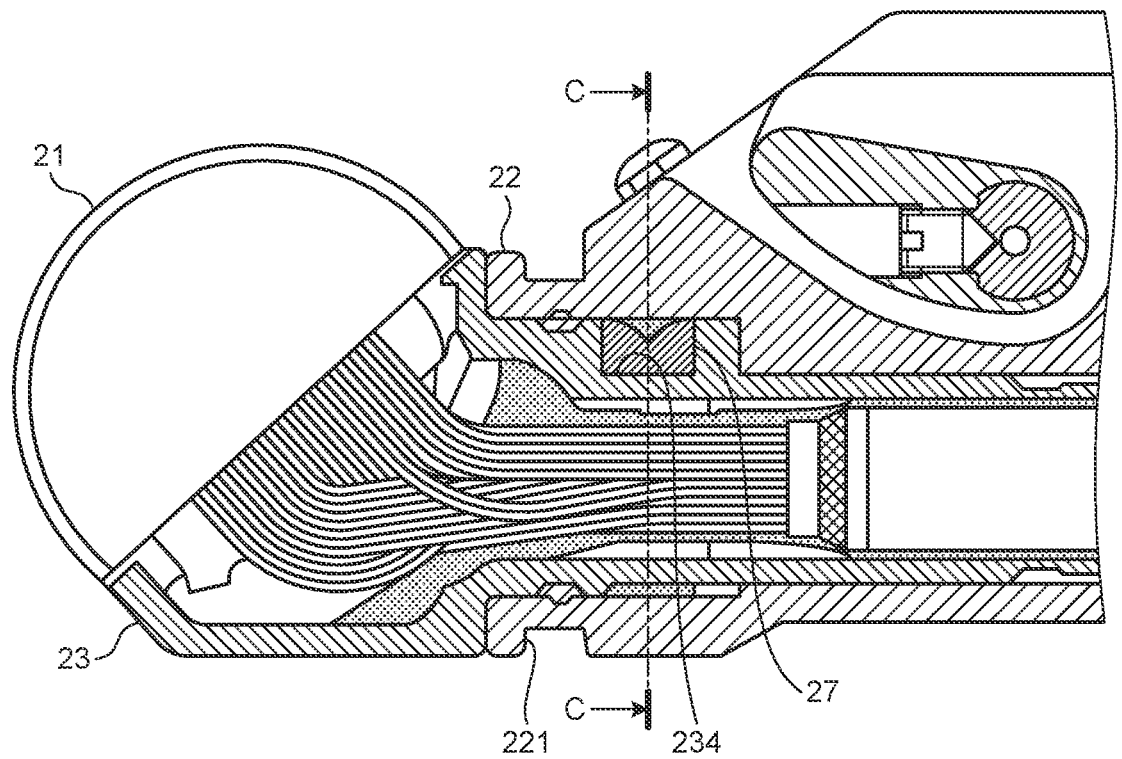
FIG. 12 is a sectional view of a distal end portion.

FIG. 12 is a sectional view of a distal end portion. As illustrated in FIG. 12, the holder 23 has a groove 234 formed on the proximal end side of the balloon groove 221 and a screw receiver 27 has been fitted in this groove 234. Positioning the screw receiver 27 on the proximal end side of the balloon groove 221 enables reduction in rigid length (length of a portion that does not have flexibility and is rigid) at the distal end of the insertion portion 2 and reduction in strain on the patient.

Figure 13:
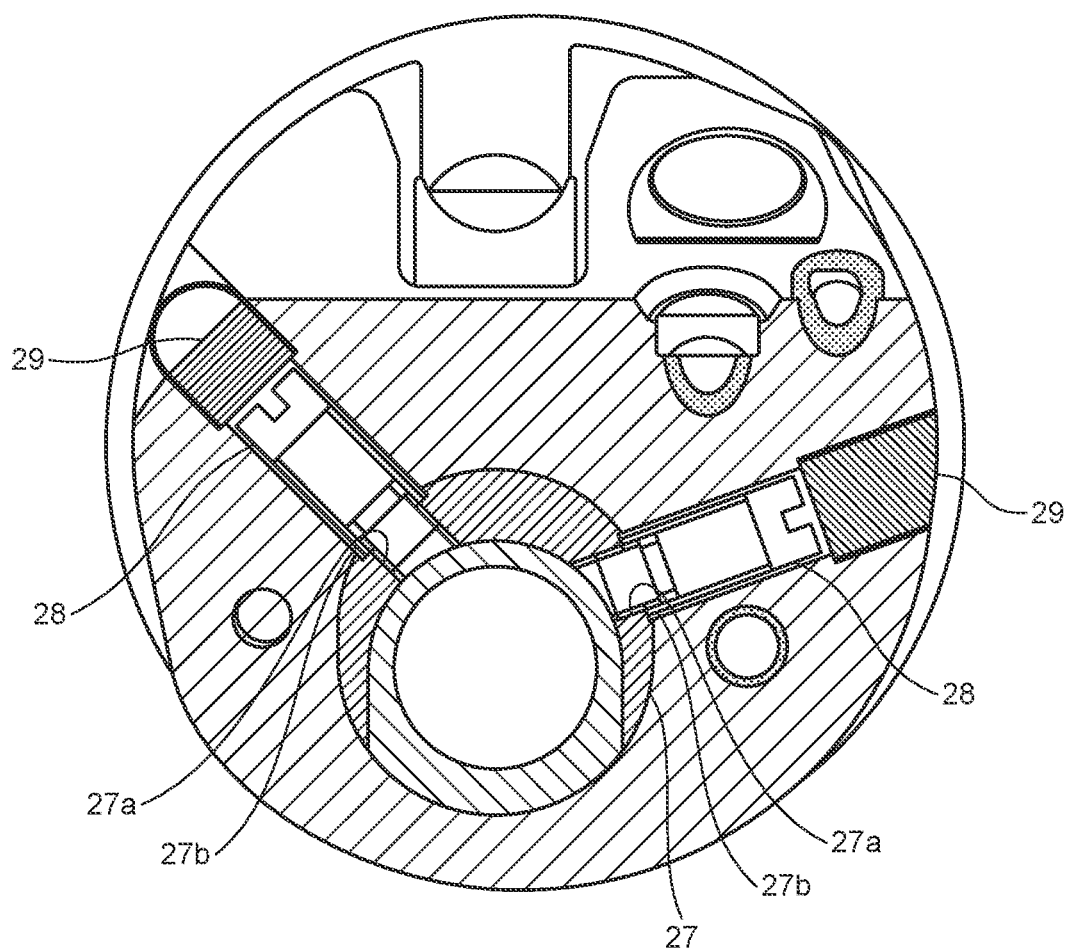
FIG. 13 is a sectional view corresponding to a line C-C in FIG. 12.

FIG. 13 is a sectional view corresponding to a line C-C in FIG. 12. As illustrated in FIG. 13, screwing fixing screws 28 into the screw receiver 27 fixes the holder 23 to the rigid portion 22. Furthermore, the fixing screws 28 are sealed by fillers 29.

Figure 14:
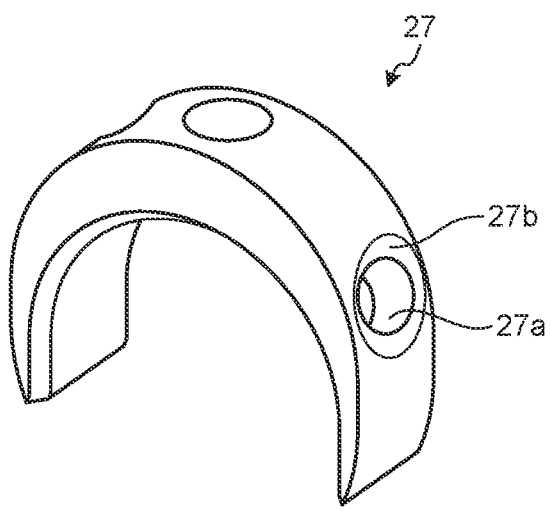
FIG. 14 is an enlarged perspective view of a screw receiver.

FIG. 14 is an enlarged perspective view of a screw receiver. As illustrated in FIG. 14, the screw receiver 27 has, formed therein, female screws portions 27a where the fixing screws 28 are screwed into, and screw receiving portions 27b that come into contact with the fixing screws 28. The screw receiver 27 is made of, for example, metal or alloy.

Figure 15:
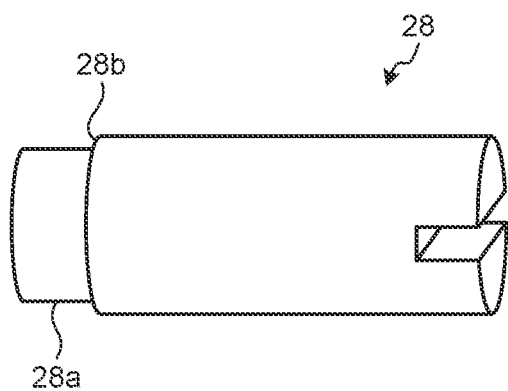
FIG. 15 is an enlarged view of a fixing screw.

FIG. 15 is an enlarged view of a fixing screw. As illustrated in FIG. 15, each of the fixing screws 28 has, formed therein, a male screw portion 28a that is screwed into the female screw portion 27a and an abutting surface 28b that comes into contact with the screw receiving portion 27b. The male screw portion 28a and the abutting surface 28b of each of the fixing screws 28 have been formed integrally with each other. The fixing screws 28 are made of, for example, metal or alloy.

Screwing the fixing screw into the screw receiver 27 causes the abutting surface 28b to come into contact with the screw receiving portion 27b. As a result, the screw receiver 27 and fixing screw 28, which are metallic, come into contact with each other and are thus firmly fastened to each other. Furthermore, a distal end of the fixing screw 28 is prevented from coming into contact with the holder 23 and causing distortion, for example.

Figure 16:
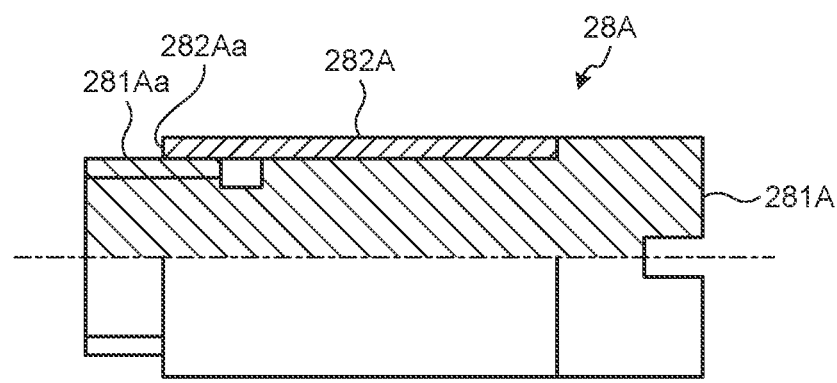
FIG. 16 is a sectional view of a fixing screw.

FIG. 16 is a sectional view of a fixing screw. As illustrated in FIG. 16, a fixing screw 28A has a screw 281A where a male screw portion 281Aa has been formed, and a sleeve 282A where an abutting surface 282Aa has been formed. The sleeve 282A for abutting may be fixed to the outer periphery of the screw 281A, as illustrated.

Figure 17:
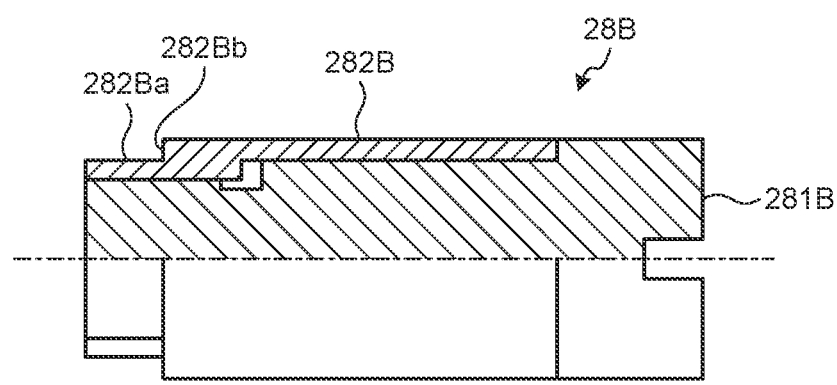
FIG. 17 is a sectional view of a fixing screw.

FIG. 17 is a sectional view of a fixing screw. As illustrated in FIG. 17, a fixing screw 28B has a screw 281B, and a sleeve 282B where a male screw portion 282Ba and an abutting surface 282Bb have been formed. The sleeve 282B for screwing and abutting may be fixed to the outer periphery of the screw 281B, as illustrated.

The disclosure enables an ultrasound endoscope to be provided, the ultrasound endoscope enabling: improvement in workability for washing of the balloon suction duct; and prevention of failure of balloon deflation.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound endoscope, comprising:
   a first duct provided inside an insertion portion;
   a rigid portion comprising:
      a balloon groove configured to accept a band of a balloon, and
      a first surface positioned distally relative to the balloon groove, the first surface intersecting a longitudinal direction of the insertion portion, the first surface having a first opening communicating with the first duct; and
   a casing positioned distally relative to the rigid portion, the casing configured to hold an ultrasound transducer;
   wherein a distal portion of the first duct overlaps a proximal portion of the casing in a longitudinal direction of the rigid portion,
   the rigid portion further comprising a second duct configured to feed liquid into the balloon covering the ultrasound transducer, and
   the second duct having a second opening on the first surface.

2. The ultrasound endoscope according to claim 1, wherein the casing includes an external surface, and at least part of the first surface extends radially outward relative to the external surface.

3. The ultrasound endoscope according to claim 1, wherein the casing includes an external surface, and at least part of the first opening is positioned radially outward relative to the external surface.

4. The ultrasound endoscope according to claim 1, wherein the casing includes an external surface, the external surface and the first surface together define a space, and wherein the first opening of the first duct is in fluid communication with the space.

5. The ultrasound endoscope according to claim 4, wherein
   the external surface has a second surface extending along the longitudinal direction of the rigid portion and a third surface continuous with the second surface, the third surface extending proximally and radially inward from the second surface, and
   the space is formed between the first surface, and the third surface.

6. The ultrasound endoscope according to claim 5, wherein an angle between the first surface and the third surface is at least 60°.

7. The ultrasound endoscope according to claim 5, wherein the space is continuous along a direction orthogonal to both of the longitudinal direction of the rigid portion and a direction in which the first duct extends.

8. The ultrasound endoscope according to claim 4, wherein an entirety of the space is offset radially from a central longitudinal axis of the insertion portion.

9. The ultrasound endoscope according to claim 4, wherein the first surface and the external surface intersect to form the space.

10. The ultrasound endoscope according to claim 1, wherein the first opening is open in a plane along a direction intersecting the longitudinal direction of the insertion portion.

11. The ultrasound endoscope according to claim 1, further comprising a fourth surface radially offset from the first surface relative to the longitudinal direction of the insertion portion, wherein the first opening and the second duct having a second opening on the fourth surface.

12. The ultrasound endoscope according to claim 1, further comprising the balloon, the balloon covering the ultrasound transducer positioned at a distal end of the insertion portion.

13. The ultrasound endoscope according to claim 1, wherein the casing includes:
- a distal end portion having a first outer diameter; and
- a proximal end portion having a second outer diameter smaller than the first outer diameter, the proximal end portion arranged adjacently to the first opening.

14. The ultrasound endoscope according to claim 1, wherein the first duct is configured to suction liquid inside the balloon.

15. The ultrasound endoscope according to claim 1, wherein the rigid portion comprises a projection, the first surface is a distal end surface of the projection.

16. The ultrasound endoscope according to claim 15, wherein an entirety of the projection is offset radially from a central longitudinal axis of the insertion portion.

17. The ultrasound endoscope according to claim 1, wherein the first opening of the first duct is offset radially from the longitudinal axis of the insertion portion.

18. The ultrasound endoscope according to claim 1, wherein the casing is fixed to the rigid portion.

\* \* \* \* \*